(12) United States Patent
Kim

(10) Patent No.: US 9,763,988 B2
(45) Date of Patent: Sep. 19, 2017

(54) NANO-SIZED KIMCHI LACTIC ACID BACTERIA

(71) Applicant: BIOGENICS KOREA CO., LTD., Seoul (KR)

(72) Inventor: Hyunung Kim, Seoul (KR)

(73) Assignee: BIOGENICS KOREA CO., LTD., Seoul (KR)

( * ) Notice: Subject to any disclaimer, the term of this patent is extended or adjusted under 35 U.S.C. 154(b) by 0 days.

(21) Appl. No.: 14/780,123

(22) PCT Filed: May 31, 2013

(86) PCT No.: PCT/KR2013/004846
§ 371 (c)(1),
(2) Date: Sep. 25, 2015

(87) PCT Pub. No.: WO2014/193014
PCT Pub. Date: Dec. 4, 2014

(65) Prior Publication Data
US 2016/0074443 A1    Mar. 17, 2016

(30) Foreign Application Priority Data

May 29, 2013  (KR) ......................... 10-2013-0061200

(51) Int. Cl.
| | | |
|---|---|---|
| *A61K 35/00* | (2006.01) | |
| *A61K 35/747* | (2015.01) | |
| *C12N 1/20* | (2006.01) | |
| *C12R 1/25* | (2006.01) | |
| *A61K 35/74* | (2015.01) | |
| *A23L 19/20* | (2016.01) | |
| *A23L 33/135* | (2016.01) | |

(52) U.S. Cl.
CPC ............ *A61K 35/747* (2013.01); *A23L 19/20* (2016.08); *A23L 33/135* (2016.08); *A61K 35/74* (2013.01); *C12N 1/20* (2013.01); *C12R 1/25* (2013.01); *A23V 2002/00* (2013.01); *A23Y 2220/67* (2013.01)

(58) Field of Classification Search
None
See application file for complete search history.

(56) References Cited

U.S. PATENT DOCUMENTS

| 2011/0117629 A1 | 5/2011 | Lin et al. |
| 2011/0189343 A1* | 8/2011 | Hasegawa ............... A61K 8/99 |
| | | 426/61 |

FOREIGN PATENT DOCUMENTS

| KR | 100413335 | 12/2003 |
| KR | 100771209 | 10/2007 |
| KR | 1020090040025 | 4/2009 |
| KR | 1020090086796 | 8/2009 |
| KR | 1020110000871 | 1/2011 |
| KR | 101068531 | 9/2011 |

OTHER PUBLICATIONS

Yang et al., International Journal of Food Microbiology, 2010, vol. 139, p. 56-63.*
International Search Report—PCT/KR2013/004846 dated Feb. 24, 2014.
Kim, Superiority of Nano-sized Lactic Acid Bacteria nF1, 2012 International Fermentation Technology Seminar, Oct. 26, 2012, p. 12.
Korean Office Action—Korean Application No. 10-2013-0061200 dated Aug. 27, 2015, citing KR 10-2009-0040025 and GenBank Accession No. AB601179.
Korean Office Action—Korean Application No. 10-2013-0061200 dated Jan. 28, 2015, citing KR 10-2011-0000871 and GenBank Accession No. AB601179.
NCBI, GenBank Accession No. AB601179.1, *Lactobacillus plantarum* subsp. *plantarum* gene for 16S rRNA, partial sequence, strain: Ni729, May 8, 2012.
NCBI, GenBank Accession No. AB725347.1, *Lactobacillus plantarum* gene for 16S rRNA, partial sequence, strain: Nf1, Jun. 2, 2012.

* cited by examiner

*Primary Examiner* — Kade Ariani
(74) *Attorney, Agent, or Firm* — Cantor Colburn LLP

(57) ABSTRACT

A nano-sized *Lactobacillus plantarum* (*L. plantarum*) nF1 strain isolated from kimchi and which has a particle size distribution of 0.5 to 1.0 μm. Pharmaceutical compositions and functional food compositions comprising the nano-sized *L. plantarum* nF1 strain may be used to prevent and treat colorectal diseases including colitis and colorectal cancer.

10 Claims, 14 Drawing Sheets

NANO-SIZED KIMCHI LACTIC ACID BACTERIA

TECHNICAL FIELD

This invention relates to nano-sized kimchi lactic acid bacteria, and more particularly, to lactic acid bacteria, i.e., *Lactobacillus plantarum* (*L. plantarum*) isolated from kimchi having an excellent effect of improving an intestinal environment.

BACKGROUND ART

Lactic acid bacteria, also called "*Lactobacillus*", are bacteria producing lactic acid by decomposing saccharides such as glucose, and have a property of inhibiting the growth of pathogens and harmful bacteria by lactic acid generated by lactic acid fermentation so as to be used in the production of foods such as dairy products, kimchi, brewed products, etc. In addition, lactic acid bacteria have been used to inhabit an intestine of a mammal to prevent abnormal fermentation by putrefactive bacteria, and thus has been used as a digestive. The lactic acid bacteria are gram-positive, and facultative anaerobic or anaerobic, and various types of *Lactobacillus* genus and *Streptococcus* genus have been known.

Kimchi is a traditional Korean food fermented by lactic acid bacteria, and lactic acid bacteria isolated from kimchi include *Leuconostoc mesenteroides, Leuconostoc dextranicum, Lactobacillus brevis, Lactobacillus plantarum*, and *Pediococcus pentosacues*.

Patents relating to lactic acid bacteria isolated from kimchi include Korean Patent No. 413335 relating to *Lactobacillus lactis* BH5 which are lactic acid bacteria producing an antibacterial peptide material, Korean Patent No. 771209 relating to *L. plantarum* having an excellent antioxidant activity, and Korean Patent No. 1068531 relating to a lactic acid bacterial strain producing bacteriocin.

However, all of the conventionally disclosed kimchi lactic acid bacteria relate to probiotics, are drastically decreased in vial cell counts in an intestinal environment and not absorbed in an intestine when taken as a food, thereby degrading a true effect. Moreover, since strains able to be grown in a predetermined volume of a culture solution are limited, it have a problem of a limited daily intake.

SUMMARY OF INVENTION

Technical Problem

Therefore, the object of the present invention is to solve the above problem by identifying lactic acid bacteria having the most excellent effect of improving an intestinal environment among lactic acid bacteria isolated from kimchi, and providing them as nano-sized kimchi lactic acid bacteria.

Solution to Problem

To achieve the object, the present invention provides a new *L. plantarum* strain isolated from kimchi.

The present invention also provides a food additive including the *L. plantarum* strain or a culture supernatant thereof as an active ingredient.

The present invention also provides a pharmaceutical composition for preventing and treating a colorectal disease including the *L. plantarum* strain or the culture supernatant thereof as an active ingredient.

The present invention also provides a method of producing nano-sized kimchi lactic acid bacteria from the *L. plantarum* strain.

The present invention also provides nano-sized kimchi lactic acid bacteria produced from the *L. plantarum* strain.

The present invention also provides a food additive or fermented food including the nano-sized kimchi lactic acid bacteria.

The present invention also provides a pharmaceutical composition for preventing and treating a colorectal disease including the nano-sized kimchi lactic acid bacteria.

The present invention also provides a health functional food composition for preventing and treating a colorectal disease including the nano-sized kimchi lactic acid bacteria.

Advantageous Effects of Invention

Nano-sized kimchi lactic acid bacteria according to the present invention have an effect of inhibiting intestinal putrefactive bacteria and an effect of improving an intestinal environment through activation of an immune function, and an excellent effect of preventing and treating colorectal diseases including colitis and colorectal cancer. In addition, the nano-sized kimchi lactic acid bacteria consist of uniform particles to facilitate intestinal absorption, and thus the effect of improving an intestinal environment is proportionally increased according to a concentration.

In addition, the nano-sized kimchi lactic acid bacteria according to the present invention are used as a food additive to provide all of the effects of the lactic acid bacteria, and thus, due to high thermal resistance, although added to a food to be heated, the nano-sized kimchi lactic acid bacteria still have the effects.

DETAILED DESCRIPTION OF EMBODIMENT

Figure 1:
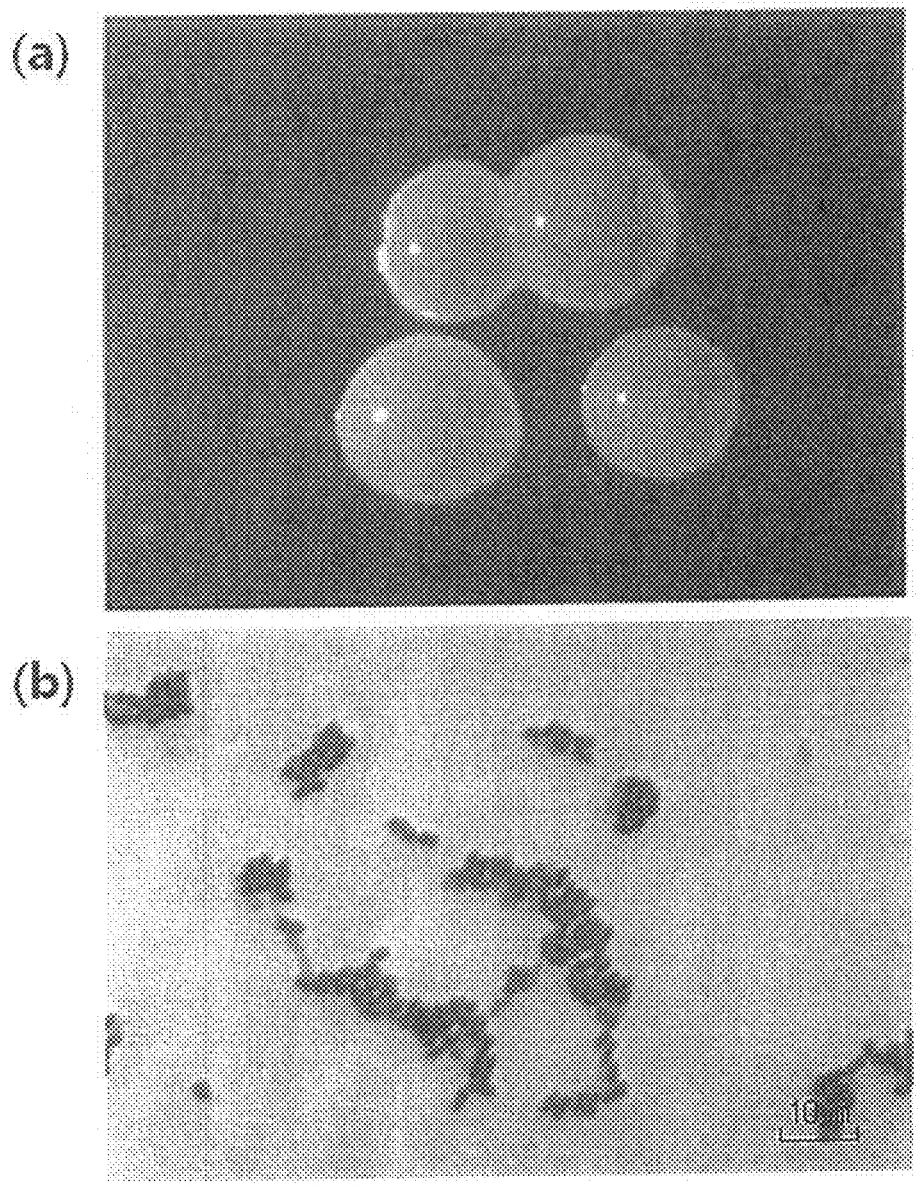
FIG. 1 is (a) an image of colonies of kimchi lactic acid bacteria of the present invention and (b) an image of the kimchi lactic acid bacteria of the present invention observed by gram staining.

Hereinafter, the present invention will be described in detail.

The present invention provides a new *L. plantarum* stain isolated from kimchi.

The inventors screened microorganisms having the most excellent effect of improving an intestinal environment by isolating *lactobacillus* from kimchi, and as the result of identification, the microorganisms were revealed as gram-positive and *bacillus*-type *L. plantarum*. The new strain was deposited as "nF1" in National Institute of Technology and Evaluation (NITE) International Patent Organism Depositary (IPOD) on Nov. 8, 2012 (NITE P-1462). It was confirmed that the strain has effects of inhibiting intestinal putrefactive bacteria, improving an intestinal environment through activation of an immune function, and preventing and treating colorectal diseases including colitis and colorectal cancer.

In addition, the present invention provides a food additive including the *L. plantarum* strain or a culture supernatant thereof as an active ingredient.

When the kimchi lactic acid bacteria or the culture supernatant thereof is used as a food additive, the kimchi-derived lactic acid bacteria may be added alone or combined with another food or food component, and may be properly used according to a conventional method. A mixed amount of the active ingredient may be suitably determined according to a purpose of use (prevention, health or therapeutic treatment). There is no particular limit to a type of the food. Examples of foods capable of including the *L. plantarum* strain or the culture supernatant thereof of the present invention may include meat, sausages, bread, chocolate, candies, cookies, snacks, pizza, ramen, other kinds of noodles, gums, dairy products including ice cream, various kinds of soup, beverages, teas, drinks, healthy beverages, alcoholic beverages and vitamin complexes, and in an acceptable meaning, also include a healthy food.

In addition, the present invention provides a pharmaceutical composition for preventing and treating a colorectal disease which includes the *L. plantarum* strain or the culture supernatant thereof as an active ingredient.

The colorectal disease may include colitis or colorectal cancer, but the present invention is not limited thereto.

The pharmaceutical composition for preventing and treating a colorectal disease including the *L. plantarum* strain or the culture supernatant thereof as an active ingredient according to the present invention may be administered orally or parenterally in a clinical administration, and may be prepared as a composition in a conventionally pharmaceutical dosage form by adding one or two or more conventional pharmaceutically available carriers or additives to an effective amount of the *L. plantarum* strain or the culture supernatant thereof as a main component.

As the carrier, one or two or more selected from a diluent, a lubricant, a binder, a disintegrating agent, a sweetening agent, a stabilizer, and a preservative may be used, and as the additive, one or two or more selected from flavors, vitamins, and an antioxidant may be used.

In the present invention, any of the pharmaceutically available carriers and the additives can be used, and particularly, the diluent may be lactose, corn starch, soybean oil, microcrystalline cellulose or mannitol, the lubricant may be magnesium stearate or talc, and the binder may be selected from polyvinylpyrrolidone (PVP) and hydroxypropylcellulose (HPC). In addition, the disintegrating agent may be selected from calcium carboxymethylcellulose (Ca-CMC), sodium starch glycolate, polacrilin potassium and crospovidone, the sweetener may be selected from sucrose, fructose, sorbitol and aspartame, the stabilizer may be selected from sodium carboxymethylcellulose (Ma-CMC), beta-cyclodextrin, white beeswax and xanthan gum, and the preservative may be selected from methyl parahydroxybenzoate, propyl parahydroxybenzoate, and potassium sorbate.

The pharmaceutical composition of the present invention may be prepared in any dosage formulation which is used to effectively treat or prevent a colorectal disease, without any particular limitation, and the formulation may be a beverage, a powder, a capsule, a soft capsule, a tablet, a gum, a pressure-sensitive adhesive type liquid preparation, a formulation for transdermal administration such as a lotion, a salve, a gel, a cream, a patch or a spray, or a herbal tea-type pharmaceutical such as a pill, a tablet, a powder or a granule.

The pharmaceutical composition of the present invention may include vitamin B, C, E or beta carotene, a compound containing a mineral such as Ca, Mg or Zn, a phospholipid such as lecithin, or a compound such as maltol, an oligosaccharide or amino acid as an auxiliary component, in addition to the main component, and among these, a mixture of two to three components of vitamins C and E, beta carotene and maltol is preferably used to reinforce bioactivity.

In addition, to stimulate the palate, a mixture of a known additive, for example, a natural flavor or the juice of a plum, a lemon, a pineapple or herb, a natural pigment such as chlorophyllin or flavonoid, or a sweetening component such as fructose, honey, sugar-alcohol or sugar with an acidulant such as citric acid or sodium citrate may be used, in addition to the above-described components.

In addition, the present invention provides a method of producing nano-sized kimchi lactic acid bacteria from the *L. plantarum* strain.

In addition, the present invention provides nano-sized kimchi lactic acid bacteria produced from the *L. plantarum* strain.

A nano-sized kimchi lactic acid bacterial cell according to the present invention has a mode (particle size) of particle size distribution of 1.0 μm or less, and preferably, 0.5 to 1.0 μm.

In the present invention, the "mode of particle size distribution" is a value which is an index indicating a bacterial size, and also refers to a particle diameter which has the highest relative frequency in the particle size distribution when a particle diameter of the bacterial cell is measured.

A type of the nano-sized kimchi lactic acid bacterial cell of the present invention may be live or dead cells. However, since the live cells have a high possibility to be morphologically changed during shipping or display after the production of a product, dead cells that are not morphologically changed are preferably used.

It has been known that lactic acid bacteria are morphologically changed due to stress when a growth environment becomes poor. Accordingly, in the present invention, lactic acid bacteria are proliferated while maintained to have a constant bacterial shape by controlling culture and processing conditions, thereby producing nano-sized kimchi lactic acid bacteria having the above-described mode of the particle size distribution.

In addition, the "nano-sized kimchi lactic acid bacterial cells" may be dispersed.

A dispersion method may be, but is not particularly limited to, for example, a method of dispersing a cell culture solution using a high pressure homogenizer at a pressure of approximately 150 kgf/cm$^2$ (1.5 MPa) in a wet process.

In this case, a known dispersing agent or excipient may be previously added to a culture solution to effectively prevent reaggregation of bacterial cells. Amounts of the added dispersing agent and excipient may vary depending on a functional activity of the bacterial cells, and is preferably 1 to 100 folds, and more preferably, 2 to 20 folds based on mass according the bacterial cells. As a suitable dispersing agent and excipient, trehalose, dextrin, or skim milk may be used.

In addition, to finally obtain the "nano-sized kimchi lactic acid bacterial cells" of the present invention in the form of a powder, a known dispersing agent excipient is added to a culture solution to disperse the bacterial cells to prevent reaggregation, and then freeze-drying and spray drying may be performed. As a result, a bacterial cell powder having excellent dispersity in water may be obtained.

The above-described nano-sized kimchi lactic acid bacterial cells of the present invention are micronized to a particle size of 1.0 μm or less.

Moreover, the bacterial cells may be prepared in a dry powder by the above method, and even though the powder is resuspended in a physiological digestive fluid, the particle size of the bacterial cell is maintained at 1.0 μm or less. The physiological digestive fluid refers to an artificial gastric fluid or intestinal fluid prepared by a known method.

According to the amount of the dispersing agent or excipient added in the production of the nano-sized kimchi lactic acid bacteria of the present invention, a concentration of kimchi lactic acid bacteria *L. plantarum* stains per 1 g of the dry powder may be controlled. The present invention is characterized by including $10^8$ to $5 \times 10^{12}$ lactic acid bacterial strains, preferably, $10^{12}$ to $5 \times 10^{12}$ lactic acid bacterial strains per 1 g of the nano-sized kimchi lactic acid bacteria powder of the present invention.

While the nano-sized kimchi lactic acid bacterial cells of the present invention may be commercialized as they are, generally, a final product may be made by adding and blending various additives or flavors to the bacterial cells to improve flavor and taste or may be manufactured in a necessary shape.

Specifically, the present invention provides a food additive or fermented food including the nano-sized kimchi lactic acid bacteria.

Specifically, as components added and mixed to the nano-sized kimchi lactic acid bacteria of the present invention, various types of carbohydrates or emulsifiers, sweeteners, acidulants, and fruit juice may be used. More particularly, the nano-sized kimchi lactic acid bacterial composition may be obtained by blending sugars such as glucose, sucrose, fructose, honey, etc.; sugar-alcohols such as sorbitol, xylitol, erythritol, lactitol, palatinit, etc.; or emulsifiers such as a sucrose fatty acid ester, a glycerin fatty acid ester, lecithin, etc. The nano-sized kimchi lactic acid bacterial composition may have excellent flavor and taste by blending various vitamins such as vitamin A, vitamins B, vitamin C, vitamin E, etc., herb extracts, cereal components, vegetable components, or milk components.

In addition, as a flavoring, a yogurt-like, berry-like, orange-like, quince-like, perilla-like, citrus-like, apple-like, mint-like, grape-like, pear-like, custard cream-like, peach-like, melon-like, banana-like, tropical, herbal, black tea or coffee flavor may be used, and it may be used alone or in combination with at least two thereof. An amount of the added flavor may be, but is not particularly limited to, approximately 0.05 to 0.5 wt %, particularly, approximately 0.1 to 0.3 wt % of the bacterial cells in terms of flavor.

In addition, the present invention provides a pharmaceutical composition and a health functional food composition for preventing and treating a colorectal disease including the nano-sized kimchi lactic acid bacteria.

The nano-sized kimchi lactic acid bacterial cells of the present invention described above may be manufactured in any type of a product such as a solid or liquid product. Particularly, together with a pharmaceutically available salt, an excipient, a preservative, a coloring agent, and a corrigent, the nano-sized kimchi lactic acid bacterial cells may be commercialized in various types such as a beverage, a granule, a tablet and a capsule by a method known in a pharmaceutical or food manufacturing field.

In addition, the nano-sized kimchi lactic acid bacterial cells of the present invention may be used as a food composition, particularly, as a health food. The health food refers to a food manufactured for the purpose of health care, maintenance and promotion of health in a more active sense than a normal food. The type of the health food may be any one of a liquid, a semi-solid and a solid, and specifically, sweets such as cookies, grilled crepes, jelly, sweet jelly (yokan), snacks, bread or cakes, beverages such as yogurt, soft drinks, nutritional drinks, a sweet rice drink or juice, soup, ice cream, milk powder, kimchi, or ramen.

In addition, the nano-sized kimchi lactic acid bacterial cells of the present invention may be manufactured in various types of external preparations for skin care, for example, a lotion (tonic), a cosmetic cream, an emulsion, a toner, a pack, a skin milk (oil), a gel, a powder, a lip cream, lipstick, under make-up, a foundation, a sun care product, a bath product, a body shampoo, a body rinse, soap, a cleansing foam, a salve, a patch, a jelly, and an aerosol.

In addition, the nano-sized kimchi lactic acid bacterial cells of the present invention may be properly blended with various components or additives conventionally used in a cosmetic, a sanitary aid or a pharmaceutical, which will be described below, when needed.

Specifically, a moisturizer such as glycerin, vaseline, urea, hyaluronic acid or heparin; a UV absorbent•scatterer such as a PABA derivative (paraaminobenzoate, Escalol 507 (ISP Japan Co., Ltd.), etc.), a cinnamic acid derivative (neoheliopan, Parsol MCX (DSM Nutrition Japan Co., Ltd.), Sunguard B (Shiseido Co., Ltd.), etc.), a salicylic acid derivative (octylsalicylate, etc.), a benzophenone derivative (ASL-24, ASL-24S (Shonan Chemical Service Co., Ltd.), etc.), a dibenzoylmethane derivative (Parsol A, Parsol DAM (DSM Nutrition Japan, Co., Ltd.), etc.), a heterocyclic derivative (Tiuvin-based, etc.) or titanium oxide; a chelating agent such as disodium edetate, trisodium edetate, citric acid, sodium citrate, tartaric acid, sodium tartarate, lactic acid, malic acid, sodium polyphosphate, sodium metaphosphate or gluconic acid; a sebum inhibitor such as salicylic acid, sulfur, caffeine or tannin; a disinfectant such as benzalkonium chloride, benzethonium chloride or chlorohexidin gluconate; an anti-inflammatory drug such as diphenyl amine hydrochloride, tranexamic acid, guaiazulene, azulene, allantoin, hinokitiol, glycyrrhizinic acid and a salt thereof, a glycyrrhizinic acid derivative or glycyrrhetinic acid; a vitamin such as vitamin A, vitamins B (B1, B2, B6, B12, B15), folic acid, nicotinic acids, pantothenic acids, biotin, vitamin C, vitamin D (D2, D3), vitamin E, ubiquinones, or vitamin K (K1, K2, K3, K4); an amino acid and a derivative thereof such as aspartic acid, glutamic acid, alanine, lysine, glycine, glutamine, serine, cysteine, cystine, tyrosine, proline, arginine or pyrrolidone carboxylic acid; a whitening agent such as retinol, protocol acetate, magnesium ascorbic phosphate, ascorbic acid 2-glucoside, arbutin, kojic acid, ellagic acid or a placenta extract; an antioxidant such as butylhydroxytoluene, butylhydroxyanisole or propyl gallate; an astringent such as zinc chloride, zinc sulfate, phenol zinc, zinc oxide or potassium aluminum sulfate; a saccharide such as glucose, fructose, maltose, sucrose, trehalose, erythritol, mannitol, xylitol or lactitol; various plant extracts such as licorice, perennial chamomile, marronnier, saxifraga, peony, quince tree, skullcap, amur cork tree, golden thread, bluets or ginkgo leaves; an oil component, a surfactant, a thickening agent, alcohols, a powder component, or a pigment may be properly blended.

Hereinafter, the present invention will be described in further detail with reference to examples.

However, the following examples are merely provided to explain the present invention, and it will be apparent to those of ordinary skill in the art that various modifications and amendments can be made in the scope and technical idea of the present invention, and it is certain that such modifications and amendments are also included in the accompanying claims.

Example 1. Identification of New Kimchi Lactic Acid Bacteria

To develop new kimchi lactic acid bacteria, the inventors diluted a kimchi extract, and cultured the extract in an MRS agar medium (Oxoid, Hampshire, the UK) at 30° C. under an aerobic condition for 48 hours. After the culture, glossy ivory colonies which are typical types of lactic acid bacteria, were selected and screened, and the selected colonies were isolated by a method of transferring the colonies to and culturing them in a fresh medium for three cycles. Among pure-cultured lactic acid bacteria, a strain (SIID11558) having the most excellent effect of improving an intestinal environment was finally selected and identified.

Figure 2:
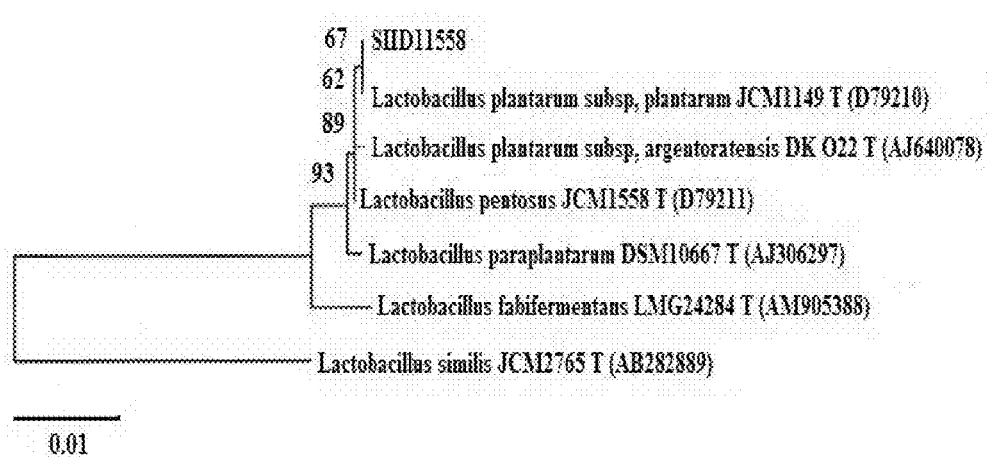
FIG. 2 is a molecular phylogenetic tree obtained by analyzing a 16S rRNA sequence of kimchi lactic acid bacteria (SIID11558) of the present invention (the bottom line on the left is a scale bar, numbers present at branches of the tree denote bootstrap values, and T at the end of a strain name denotes a type strain of the species).

As shown in FIG. 1, it was confirmed that the SIID11558 strain was a gram-positive *bacillus* forming ivory colonies and, morphologically, having a size of 0.8 to 0.9×1.2 to 1.5 µm.
Sequencing and analysis of 16S rRNA of the isolated strain were performed by Techno Suruga Laboratory Co. Ltd., and accordingly, the isolated strain was identified as a new microorganism having a high homology of 99.9% with respect to *L. plantarum*. An analyzed 16S rRNA sequence of the isolated strain was set forth in SEQ. ID. NO: 1, and a phylogenetic tree representing a phylogenetical position is shown in FIG. 2. In PCR amplification for 16S rDNA, a forward primer (5'-ga gtt tga tcc tgg ctc ag-3': SEQ. ID. NO: 2) and a reverse primer (5'-tcg taa caa ggt agc c-3': SEQ. ID. NO: 3) were used, and operations from PCR amplification to cycle sequencing were conducted based on the following protocol.

DNA extract: achromopeptidase (Wakojunyaku, Osaka)
PCR: PrimeSTAR HS DNA Polymerase (Dakarabio, Siga)
Cycle sequencing: BigDye Terminator v3.1 Cycle Sequencing Kit (Life Technologies, CA, USA)
Sequencing: ABI PRISM 3130 x1 Genetic Analyzer System (Life Technologies, CA, USA)
Sequence analysis: Chromas Pro 1.5 (Technelysium Pty Ltd., Tewantin, AUS)
BLAST homology search and simple molecular phylogenetic interpretation: Apollo 2.0 Software (Techno Suruga Lab, Shizuoka)
Database: Apollo DB-BA7.0 database (Techno Suruga Lab, Shizuoka), International Nucleotide Sequence Database (GeneBank/DDBJ/EMBL)

The new microorganism of the present invention identified by the above-described method was deposited in National Institute of Technology and Evaluation (NITE) International Patent Organism Depositary (IPOD) as "nF1" on Nov. 8, 2012 (NITE P-1462).

Example 2. Preparation of Nano-Sized Kimchi Lactic Acid Bacteria nF1 Powder

The nF1 strain isolated and identified in Example 1 was cultured in a 20 wt % sodium hydroxide aqueous solution in a known nutrient medium to which 5 wt % glucose was added, and incubated at a neutral pH and a temperature of 36.5° C. and ended at the time at which glucose started being consumed. In the preparation of nano-sized kimchi lactic acid bacteria powder of the present invention, a pH range may be a neutral region of pH 5 to 7, and most preferably pH 6.5.

Figure 3:
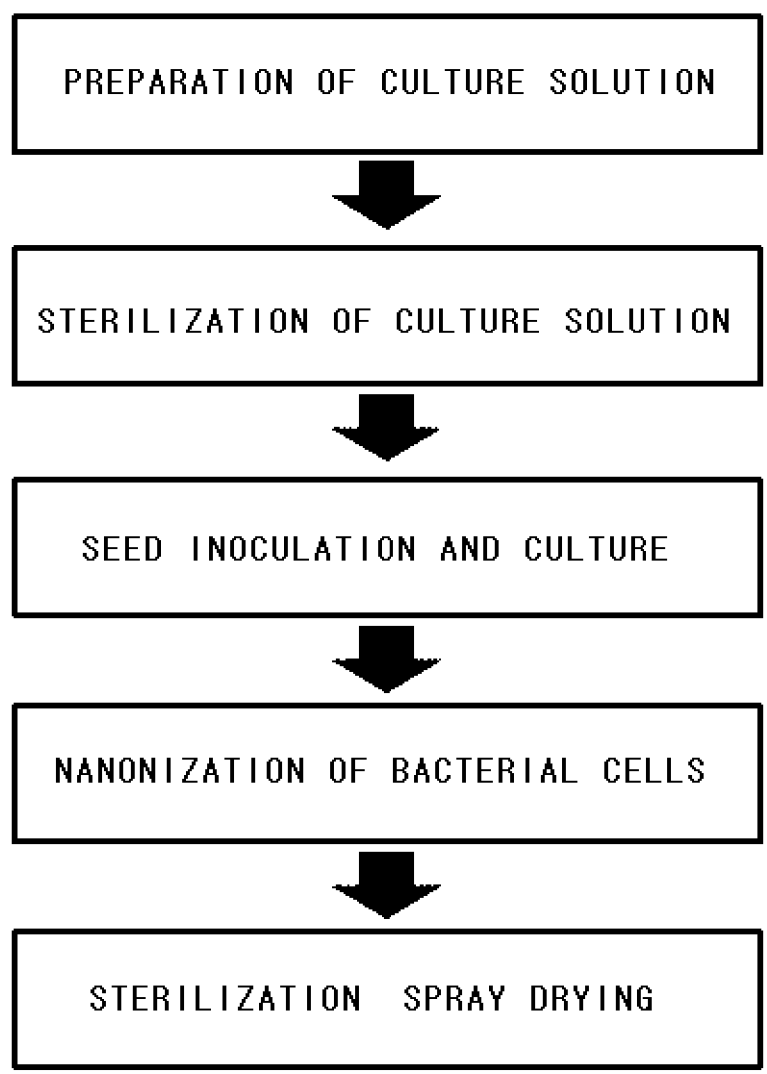
FIG. 3 is a flow chart illustrating a process of producing nano-sized kimchi lactic acid bacteria nF1 of the present invention.

After the culture, a culture solution was heated and sterilized at 80° C. for 10 minutes, the cells were washed with PBS, and dextrin was added as an excipient nine times a weight of the cells and then dispersed with a mixer. Afterward, the resulting mixture was freeze-dried through spraying to prepare a powder sample, and it was confirmed that $10^{12}$ or more kimchi lactic acid bacteria nF1 strains of the present invention per 1 g were included. A process of producing nano-sized kimchi lactic acid bacteria is simply shown in FIG. 3.

Figure 4:
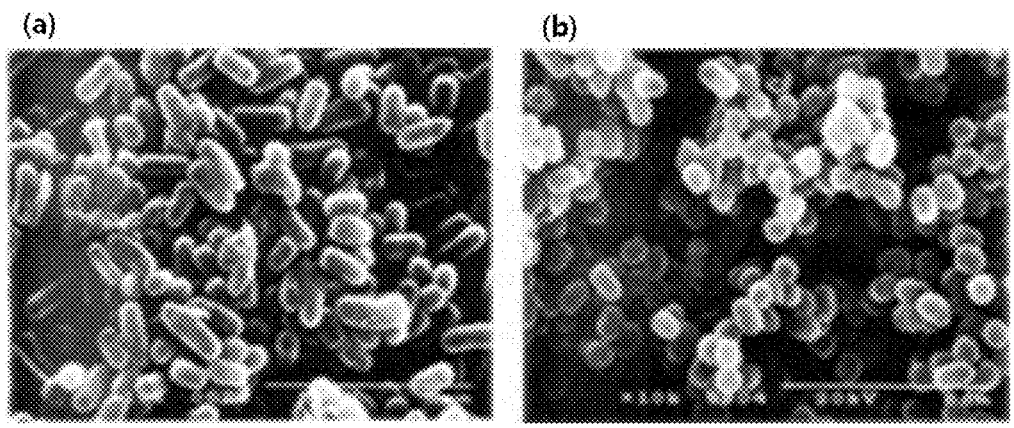
FIG. 4 shows microscope images of kimchi lactic acid bacteria of the present invention before and after nanonization: (a) before nanonization: rod shape, (b) after nanonization: spherical shape.

The nF1 powder was resuspended in PBS to adjust a cell concentration to 10 mg/ml. The pH during a processing process was maintained at 6.5. The nanonized result for the strains as described above was confirmed by a microscope, and as shown in FIG. 4, it can be noted that an nF1 strain extracted from kimchi was a rod-type *bacillus* before nanonization, but became a shape close to a coccus after the nanonization, thereby having a property in which reaggregation of colonies cannot occur. The nano-sized nF1 strain had a mode of particle size distribution of 0.5 to 1.0 µm, and was not reaggregated, thereby obtaining lactic acid bacteria having excellent dispersity in water or other solvents.

Meanwhile, to prepare the nano-sized kimchi lactic acid bacteria powder, a concentration of the lactic acid bacteria included in the powder may be controlled according to an amount of the excipient added to the bacterial cell culture solution. It was confirmed that, when the powder was prepared by adding the same amount of the dextrin as the weight of the bacterial cells, as the excipient, $5 \times 10^{12}$ kimchi lactic acid bacteria per 1 g of the prepared powder were included, and when the powder was prepared by adding dextrin four times the weight of the bacterial cells, $2 \times 10^{12}$ or more stains per 1 g were included.

Example 3. Test for Confirming Effect of Improving Intestinal Environment Using Colitis Mouse Model 3-1) Test Animal and Test Material As test animals, 6-week-old Balb/c male mice were used, and 2% dextran sulfate sodium (DSS) was administered into all groups to induce colitis, except a normal group (Normal). Specifically, mouse models were classified into the normal group (normal) in which colitis was not induced and test groups in which colitis was induced by the DSS solution, and the test groups were classified into a control group (control) into which a test material was not administered, a high concentration nF1 administered group (nF1-H), a medium concentration nF1 administered group (nF1-M), a low concentration nF1 administered group (nF1-L), a normalized kimchi administered group (N-Kimchi), and an nF1 powder-added kimchi administered group (nF1-Kimchi). As the test animals, 11 mice per each group were used, and raised at a temperature of 20±2° C., a humidity of 40 to 60% and a light and dark cycle of 12 hours.

Figure 5:
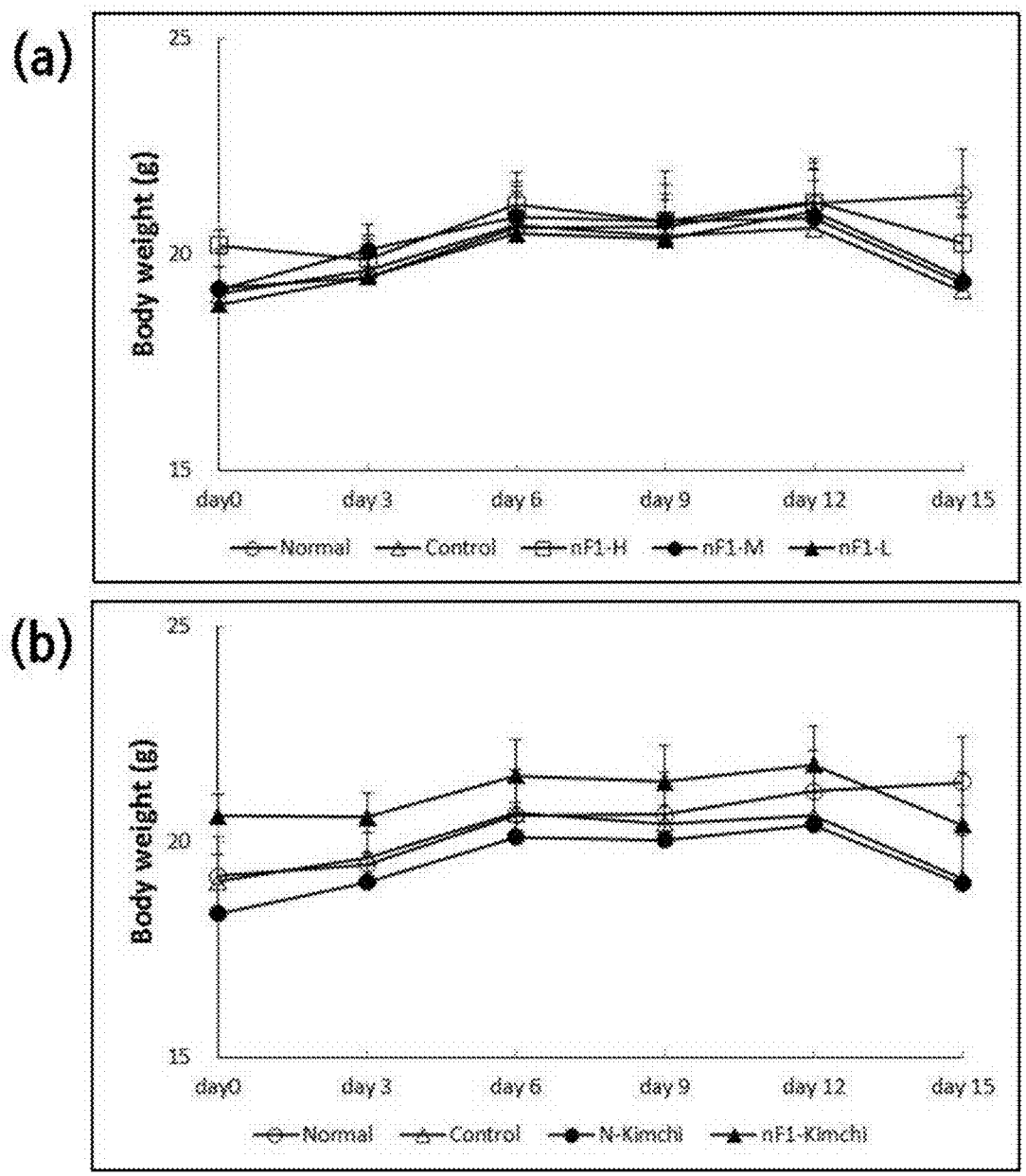
FIG. 5 is a result of measuring a change in body weight of a test model of the present invention.

As a colitis-inducing material, DSS was stirred with distilled water at a concentration of 2%, and the 2% DSS solution was provided with a negative value regardless of a body weight of a mouse to induce colitis. To maintain a colitis state right after the colitis was induced, 2% DSS was continuously provided for 7 days after being dissolved in drinking water, and the body weight of a mouse was measured every third day to confirm whether colitis was induced or not. In the normal group, a decrease in weight of a mouse was not shown during the experiment, compared to the other groups, and the body weight was highest at the time of ending the experiment (15th day). The other groups all showed similar changes in weight (refer to FIG. 5).

In the nF1 treated group, the nano-sized kimchi lactic acid bacteria nF1 powder prepared in Example 2 was used as a test material, and the powder-phase test material was diluted in PBS to various concentrations. According to previous research data in which good results were obtained when based on 50 kg adult, a daily intake had been $10^{12}$ lactic acid bacteria, therefore, provided that the body weight of a mouse was set to 20 g, a daily intake was determined to be approximately $4 \times 10^{8}$ bacteria. $10^{12}$ bacteria were included per 1 g of the nano-sized kimchi lactic acid bacteria nF1 powder of the present invention, and thus 0.4 mg/mouse ($4 \times 10^{8}$/mouse) was set to a standard concentration (medium concentration, nF1-M), the high concentration group (nF1-H) was prepared by adding the powder at 4 mg/mouse ($4 \times 10^{9}$/mouse), and the low concentration group (nF1-L) was prepared by adding the powder at 0.04 mg/mouse ($4 \times 10^{7}$/mouse).

Two kimchi-treated groups were prepared using a normalized kimchi recipe provided by Pusan National University as kimchi to which nF1 powder was not added (N-Kimchi) and nF1 powder-added kimchi (nF1-Kimchi), and nF1 powder was added at 2 g per 1 kg of kimchi. The kimchi samples prepared as described above were aged for three weeks, a juice of the optimally aged kimchi was extracted at the time in which cell counts of the lactic acid bacteria reached $10^{7-8}$ log cfu/g, and then administered into a mouse. An amount of the administered kimchi juice extract was determined as the maximum dose (200 μl), and each of the test materials was mixed with PBS to a suitable concentration right before every single oral administration.

The test groups and test materials are summarized in the following table.

TABLE 1

| Test group | Test material | Administrated dose (g/kg) | Amount of administered solution (μl, p.o.) | Number of animals |
|---|---|---|---|---|
| Normal group | — | — | 200 | 11 |
| Control group | DSS | 2% DSS | 200 | 11 |
| nF1-H | nF1 | 2 | 200 | 11 |
| nF1-M | nF1 | 0.2 | 200 | 11 |
| nF1-L | nF1 | 0.02 | 200 | 11 |
| N-Kimchi | Normalized kimchi | 0.2 | 200 | 11 |
| nF1-KImchi | nF1-added kimchi | 0.2 | 200 | 11 |

After the administration of the test material for total two weeks was ended, an autopsy was conducted, and results for the following categories were compared.

3-2) Measurement of Change in Colon Length

A colon was taken from the mouse in which colitis was induced using DSS described in 3-1), and the length and weight of the colon were measured to investigate a change in the organ caused by inflammation related to colitis. The colitis-induced mouse had a shorter colon than a normal colon, and when ulcerative colitis occurred, due to the changed and stiffness of tissues, the weight of the colon tended to be somewhat increased. As a result, a longer length and lighter weight of the colon can be seen as an effect of preventing colitis.

Figure 6:
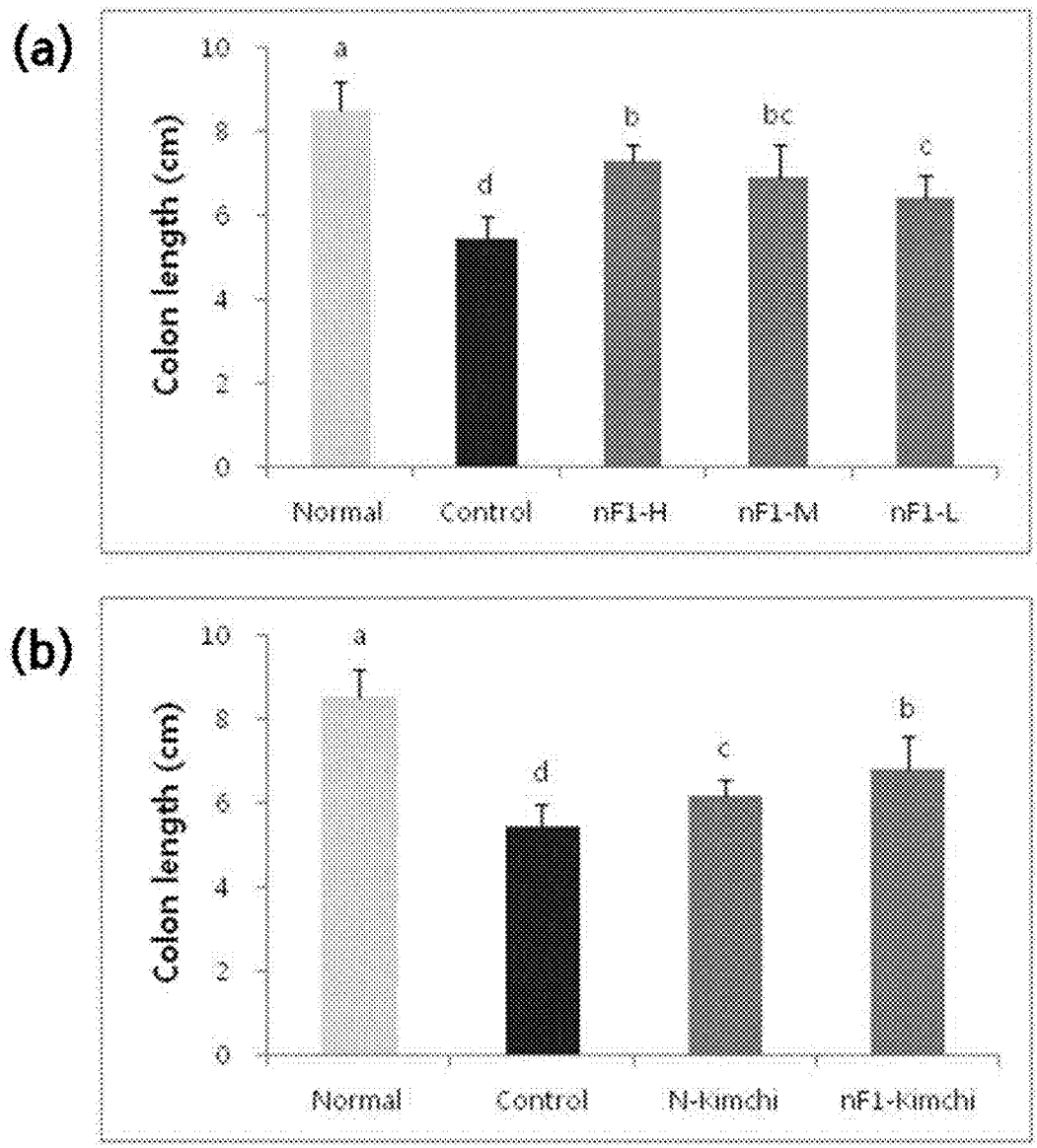
FIG. 6 shows (a) a graph showing a change in colon length of a colitis-induced mouse treated with nF1, and (b) a graph showing a change in colon length of a colitis-induced mouse into which nF1 powder-added kimchi is administered (a to d denote significant differences ($p<0.05$) according to Duncan's multiple range tests).

First, colons of the mice treated with each of the test materials were taken, and then lengths of colons of the 11 mice included in each group were represented as mean±standard deviation, which is shown in FIG. 6.

As shown in (a) in FIG. 6, since a colon length of the normal group (normal) was 8.5±0.7 cm and a colon length of the colitis-induced control group (control) was 5.7±0.6 cm, it was noted that the colon length of the control group was significantly decreased, and ulcerative colitis caused by DSS was induced ($p<0.05$).

Meanwhile, the colon lengths of the group treated with the nano-sized kimchi lactic acid bacteria nF1 of the present invention were 7.0±0.6 cm in the nF1-H group, 6.7±0.7 cm in the nF1-M group, and 6.4±0.6 cm in the nF1-L group. The nF1-H group showed the highest preventive effect, and the nF1-M and nF1-L groups had significant differences from the control group, and also had an effect of preventing colitis ($p<0.05$).

Afterward, a colon length of the mouse to which nF1-treated kimchi was administered was measured by the same method as described above, and the result is shown in (b) in FIG. 6. As shown in (b) in FIG. 6, the colon length of the normal kimchi-administered group (N-Kimchi) was 6.2±0.4 cm, and the colon length of the nF1-treated kimchi administered group (nF1-Kimchi) was 6.7±0.2 cm. It showed that, compared to the control group, these two groups had a significant effect of preventing colitis, and particularly, the nF1-Kimchi group, had a significantly higher effect of preventing colitis ($p<0.05$).

3-3) Pathological Observation of Colon Tissue

To investigate a degree of damage to a colon tissue, remaining feces in the colon of each mouse model of 3-1) were completely removed using PBS, and put into a 10% formalin solution to fix the colon under a 4° C. cold condition for 24 hours, and then a paraffin tissue sample was produced and cut into fragments 5 μm in length. The tissue fragment was stained with hematoxylin-eosin, observed at low magnification (40×) and photograph of the tissue was taken for comparison, and the result is shown in FIG. 7.

Figure 7:
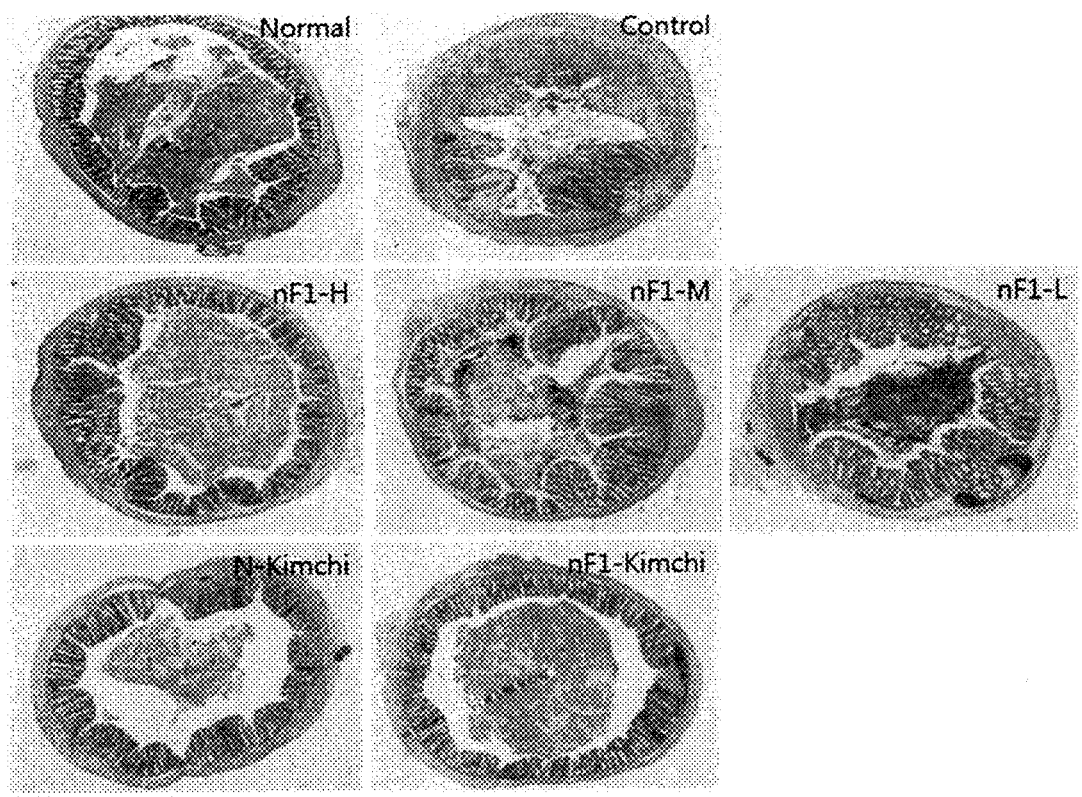
FIG. 7 shows images showing pathological observation results for colon tissues.

As shown in FIG. 7, it was observed that, compared to the normal group (normal), the control group (control) in which the ulcerative colitis was induced by DSS had damage to a mucosal layer and a submucosal layer of the colon tissue, cells in a mucous membrane and a tissue were necrotized or severely deformed by inflammation, epithelial cells on a surface of the colon tissue were eliminated, and festered crypts and an inflammatory response due to many inflammatory cells collected in the mucosal layer were observed.

Meanwhile, it was confirmed that, compared to the control group, tissues were relatively less damaged and the damage to an epithelial cell layer was reduced in the nF1-treated groups (nF1-H, nF1-M and nF1-L). Particularly, low degrees of inflammation and damage and less transformation of the tissues were observed in the nF1-H group and the nF1-M group, and such a phenomenon was more clearly shown in the nF1-H group than in the nF1-M group.

In addition, among the kimchi-treated groups, regions of inflammation were less found in the nF1-Kimchi group than the N-Kimchi group, thereby confirming that when nF1 was added to kimchi, effects of preventing and treating colitis were apparently increased.

3-4) Measurement of Expression Level of Inflammatory Cytokine in Serum

TNF-α, IL-1β, IL-6, IL-12, IFN-γ, and IL-17A are signal factors mediating inflammation, and critical molecules commonly taking charge of an inflammatory response in an immune system. A decrease in a signal factor shows that a test material has an effect of inhibiting an inflammatory response. A degree of generating an inflammation-mediating factor was observed through an expression level of inflammatory cytokine (TNF-α, IL-6, etc.) in a serum of a DSS-induced colitis model, and therefore a colitis preventive effect of nano-sized kimchi lactic acid bacteria nF1 was investigated.

Specifically, a blood sample was obtained from the mice of 3-1), each blood sample was centrifuged at 3,000 rpm for 15 minutes to separate a serum, and the secretion of cytokine such as TNF-α or IFN-γ was detected using an enzyme-linked immunosorbent assay (ELISA MAX Deluxe Sets, Biolegend). A capture antibody with respect to mouse TNF-α or IFN-γ was previously diluted in a buffer solution for coating and dispensed as 100 μl into each well of a 96-well micro plate, and then maintained overnight at 4° C. The next day, the plate was washed with a washing buffer solution four times, and 200 μl of an assay diluent was dispensed into the plate and maintained at room temperature for 1 hour. After the plate was washed four times with a washing buffer solution, 100 μl of detection antibodies were dispensed into the plate and maintained again at room temperature for 1 hour. After the plate was washed four times with a washing buffer solution, 100 μl of avidin-horseradish peroxidase (avidin-HRP) was inoculated as a target material and maintained again at room temperature for 30 minutes. After the plate was washed five times with a washing buffer solution, 100 μl of a substrate solution including a TMB substrate solution was inoculated into the plate and maintained at room temperature for 15 minutes, and then 100 μl of a stop solution was used as a treatment to stop the reaction. An optical density was measured at 450 nm using an ELISA analyzer. Results of measuring inflammatory cytokines TNF-α, IL-1β, IL-6, IL-12, IFN-γ and IL-17A are shown in FIGS. 8 and 9.

Figure 8:
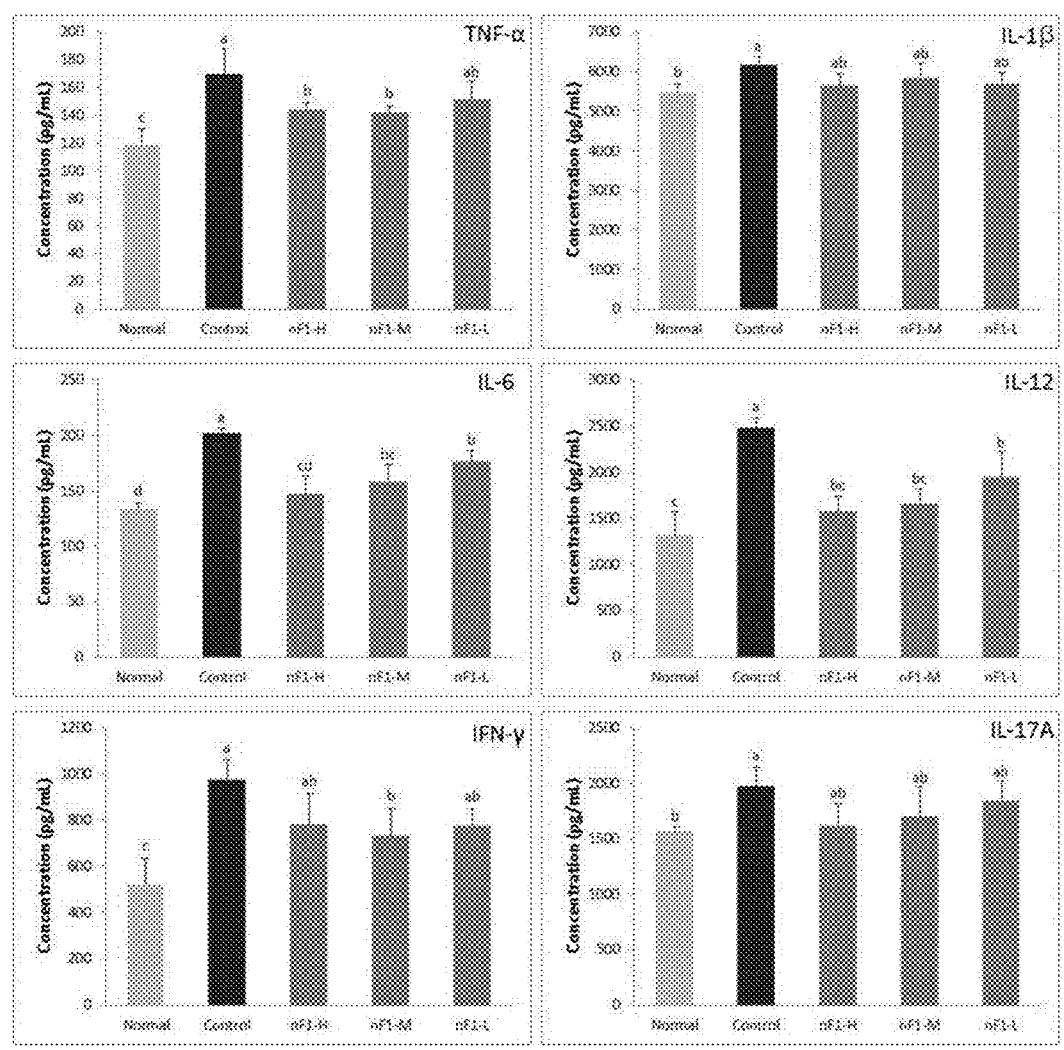
FIG. 8 shows graphs showing a change in the expression level of inflammatory cytokine of colitis-induced mice treated with nF1 (a to d denote significant differences ($p<0.05$) according to Duncan's multiple range tests).
Figure 9:
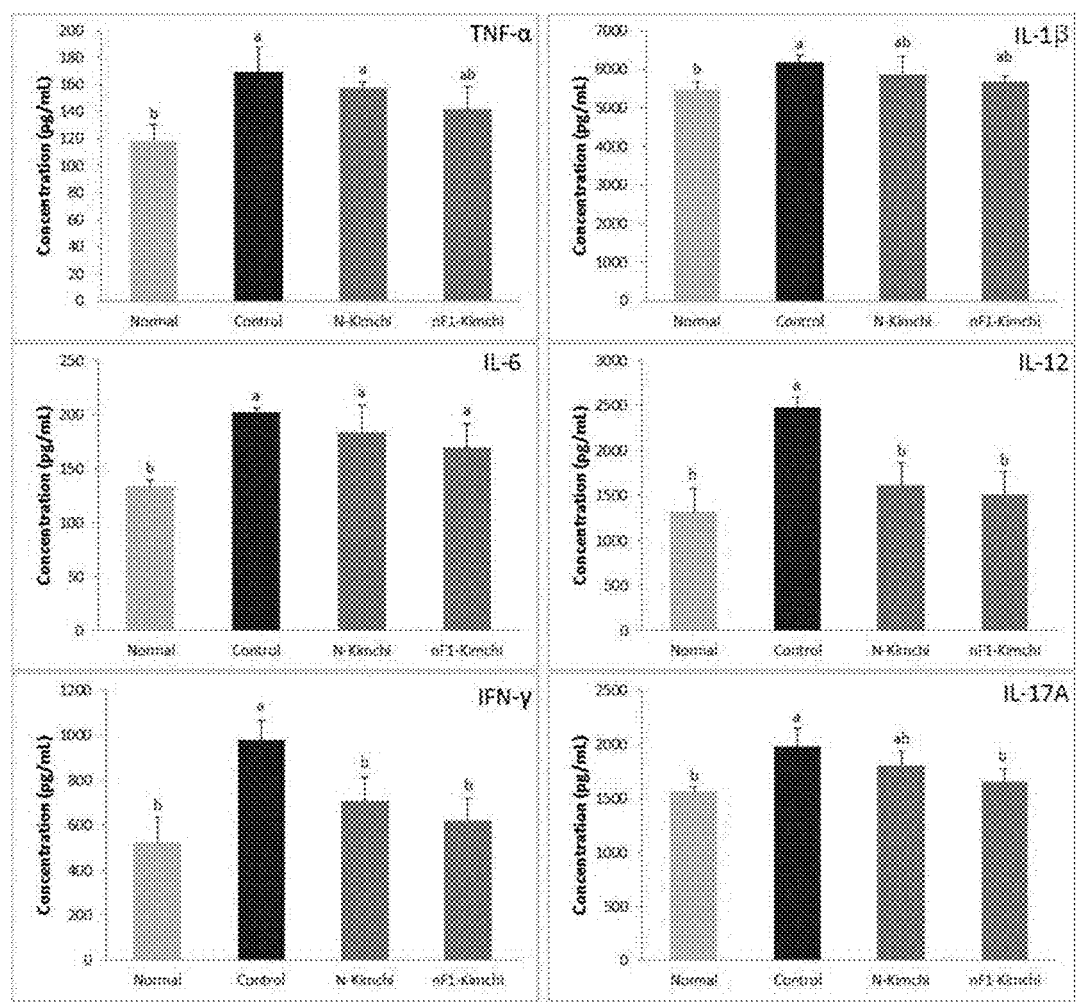
FIG. 9 shows graphs showing a change in the expression level of inflammatory cytokine of a colitis-induced mouse into which nF1 powder-added kimchi is administered (a to d denote significant differences (p<0.05) according to Duncan's multiple range tests).

Referring to FIGS. 8 and 9, the expression levels of the TNF-α, IL-1β, IL-6, IL-12, IFN-γ and IL-17A in the normal group (normal) were significantly ($p<0.05$) lower than those in the control group (control), and it was noted that, when inflammation was induced, the expression levels of such inflammatory cytokines were increased.

As shown in FIG. 8, in the mouse to which the nano-sized kimchi lactic acid bacteria nF1 was administered, the expression level of IL-6 had a significant difference ($p<0.05$) according to a concentration, and was lowest in the nF1-H group. While the expression levels of the TNF-α, IL-1β and IL-12 had no significant difference between the nF1-H group and the nF1-M group, they were significantly lower than those in the nF1-L group, the expression levels of IFN-γ and IL-17A in all of the nF1-H, nF1-M and nF1-L groups were significantly lower than those in the control group, and the expression levels in the nF1-H group were lowest. Summarizing the above results, it was seen that, compared to the control group, the expression level of the cytokines was decreased in the nF1-administered group, and particularly, as a higher concentration of nF1 was administered, the expression level of the cytokines was lower. Accordingly, it was noted that, when nF1 was taken at a high concentration, the highest colitis preventive effect was obtained.

In addition, as shown in FIG. 9, it was confirmed that the kimchi-administered mouse showed a significantly lower expression level of cytokines in the nF1-Kimchi group than in the N-Kimchi group ($p<0.05$), and therefore, it was confirmed that when nF1 was added to kimchi, the colitis preventive effect was increased.

3-5) Measurement of mRNA Expression Level of Inflammatory Cytokine in Tissue A colon tissue of a test mouse was washed with PBS and total RNA was isolated using trizol. To make mRNA of the isolated RNA into cDNA, the isolated RNA was quantified, and 2 μg of the RNA was reverse transcribed to ss cRNA complementary to mRNA using an oligo dT primer and a reverse transcriptase. Specific gene parts of TNF-α, IFN-γ, IL-6, IL-12, IL-17A, COX-2 and iNOS genes were amplified using the cDNA as a template by polymerase chain reaction (PCR). Here, as an internal control group (internal control), a housekeeping gene, GAPDH, was used. Each PCR product was analyzed by 2% agarose gel electrophoresis, stained with ethidium bromide (EtBr; Sigma, USA), and visualized under UV light. The mRNA expression levels of inflammatory cytokines (pro-inflammatory cytokines; TNF-α, IL-1β, IL-6, etc.) in a colon tissue detected by RT-PCR are shown in FIGS. 10 and 11.

Figure 10:
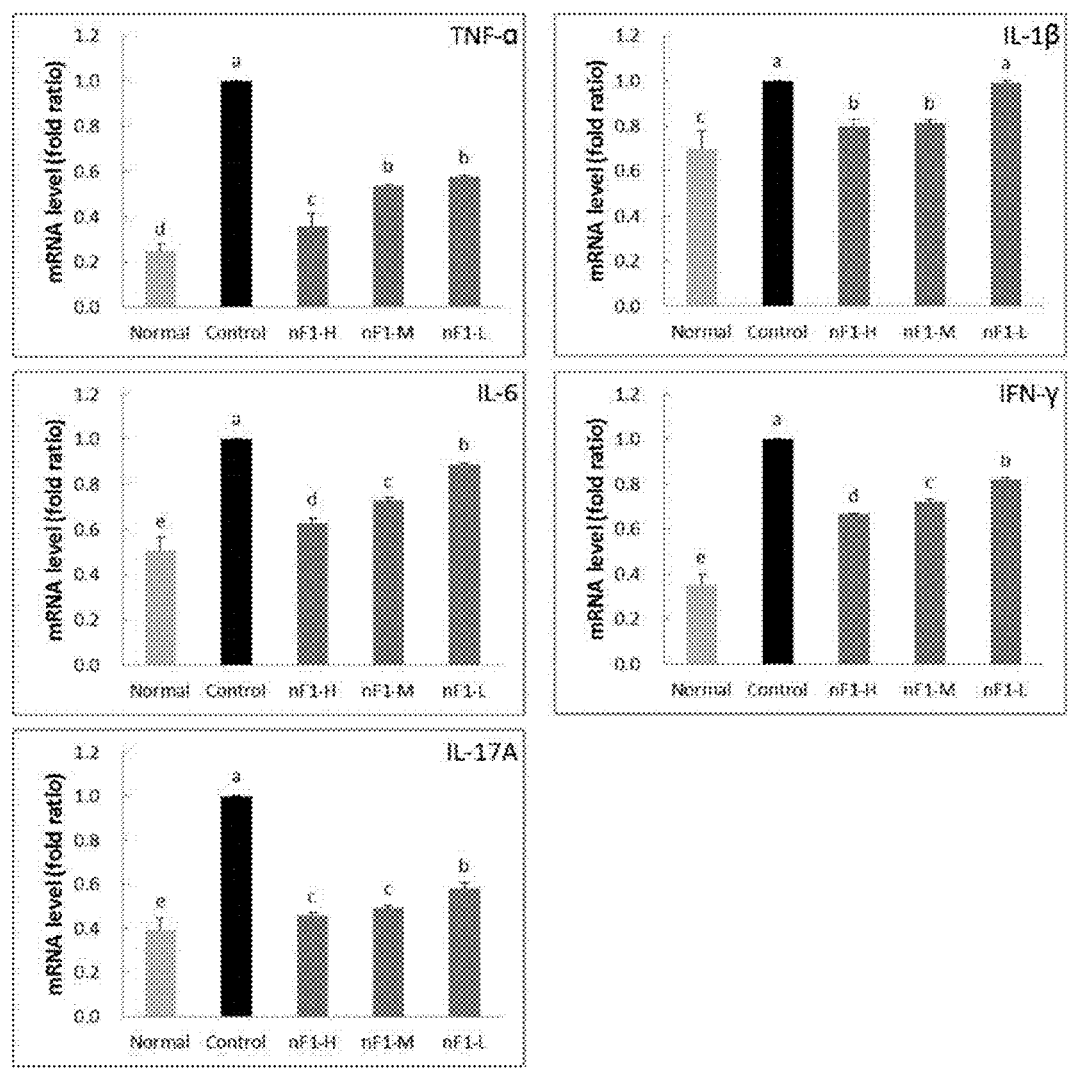
FIG. 10 shows graphs showing a change in the mRNA expression level of inflammatory cytokine of a colitis-induced mouse treated with nF1 (a to d denote significant differences (p<0.05) according to Duncan's multiple range tests).
Figure 11:
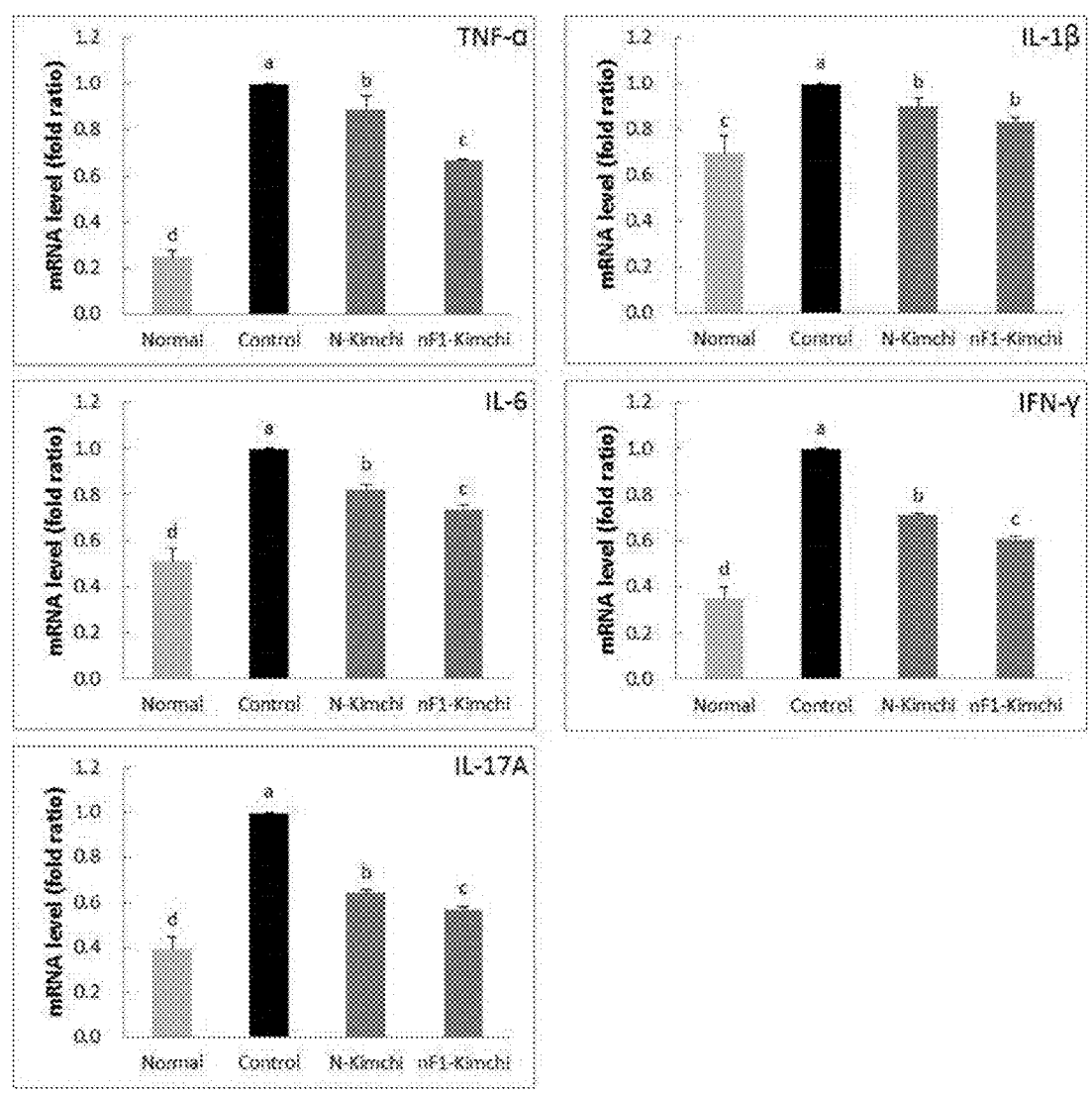
FIG. 11 shows graphs showing a change in the mRNA expression level of inflammatory cytokine of a colitis-induced mouse into which nF1 powder-added kimchi is administered (a to d denote significant differences (p<0.05) according to Duncan's multiple range tests).

Referring to FIGS. 10 and 11, compared to the normal group, the expression of TNF-α, IL-1β, IFN-γ, IL-6 and IL-17A was significantly increased in the control group ($p<0.05$), and it was noted that when colitis was induced by the expression, the mRNA expression levels of the inflammatory cytokines were increased.

Meanwhile, in the nF1-administered group, as shown in FIG. 10, as the concentration of nF1 was higher, the mRNA expression levels of TNF-α, IFN-γ, IL-6 were significantly decreased ($p<0.05$). The mRNA expression levels of IL-1β and IL-17A had no significant differences between the nF1-H group and the nF1-M group ($p<0.05$), but all were lower than those in the nF1-L group.

As shown in FIG. 11, among the kimchi-administered groups, the mRNA expression level of inflammatory cytokines in the nF1-Kimchi group was significantly lower than those in the N-Kimchi group ($p<0.05$).

Accordingly, it can be noted that when nF1 was taken at a high concentration, the highest colitis preventive effect was obtained, and it was confirmed that, when nF1 was added to kimchi, the colitis preventive effect was significantly increased.

3-6) Measurement of mRNA Expression Levels of Inflammation-Related Genes (iNOS, COX-2)

Figure 12:
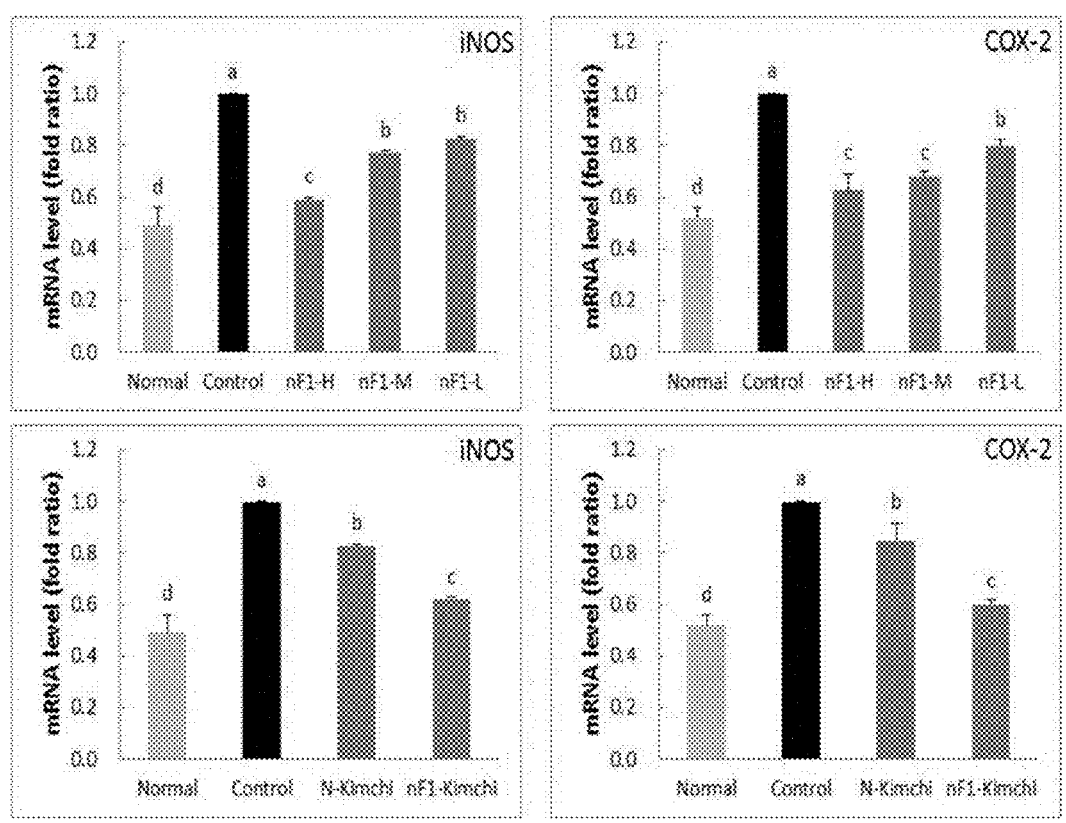
FIG. 12 shows graphs showing the mRNA expression levels of genes (iNOS and COX-2) involved in inflammation occurring in the colon of a mouse.

The mRAN expression levels of inflammation-related genes in a colon tissue, iNOS and COX-2, were analyzed by RT-PCR, and the result is shown in FIG. 12, and the expression levels of iNOS and COX-2 were similar to those of the inflammatory cytokines in Examples 3-4 and 3-5.

As shown in FIG. 12, the iNOS and COX-2 expression levels in the control group were higher than those in the normal group, and it was confirmed that as ulcerative colitis was induced, the iNOS and COX-2 expression levels were significantly increased ($p<0.05$).

Meanwhile, in the nF1-administered group, as the concentration of administered nF1 was higher, the expression levels of iNOS and COX-2 were lower, and as the administration concentration was lower, the expression levels of iNOS and COX-2 were higher, and thus there were significant differences in iNOS and COX-2 expression levels according to a concentration of administered nF1 ($p<0.05$).

In addition, comparing the nF1-Kimchi group and the N-Kimchi group, the iNOS and COX-2 expression levels in the nF1-Kimchi group were 0.62±0.00 and 0.60±0.04, respectively, and the iNOS and COX-2 expression levels in the N-Kimchi group were 0.83±0.00 and 0.85±0.01, respectively, which showed that there were significant differences between them ($p<0.05$). In nF1-added kimchi, the iNOS and COX-2 expression levels were lower than those in normal kimchi, and therefore a significantly increased colitis preventive effect was shown.

3-7) Measurement of Number of Lactic Acid Bacteria in Feces

Lactic acid bacteria in a colon have been known to reduce intestinal pH by generating an organic acid and improve an intestinal environment by inhibiting the growth of harmful bacteria. Accordingly, a change in the number of lactic acid bacteria in feces according to the administration of a test material was detected, and the results are shown in FIG. 13.

The detection of the number of the lactic acid bacteria was performed using a plate count technique. Feces of a mouse were diluted with sterilized distilled water step by step and previously dissolved with heat, dispensed in 0.1 ml each on an MRS agar plate (Difco, Detroit, Mich., USA) cooled to 43 to 45° C., and then plated. The plate was incubated in an incubator under an anaerobic condition at 37° C. for 2 days, and the number of total lactic acid bacteria was represented as colony forming units per gram (CFU/g) of the cultured bacteria.

Figure 13:
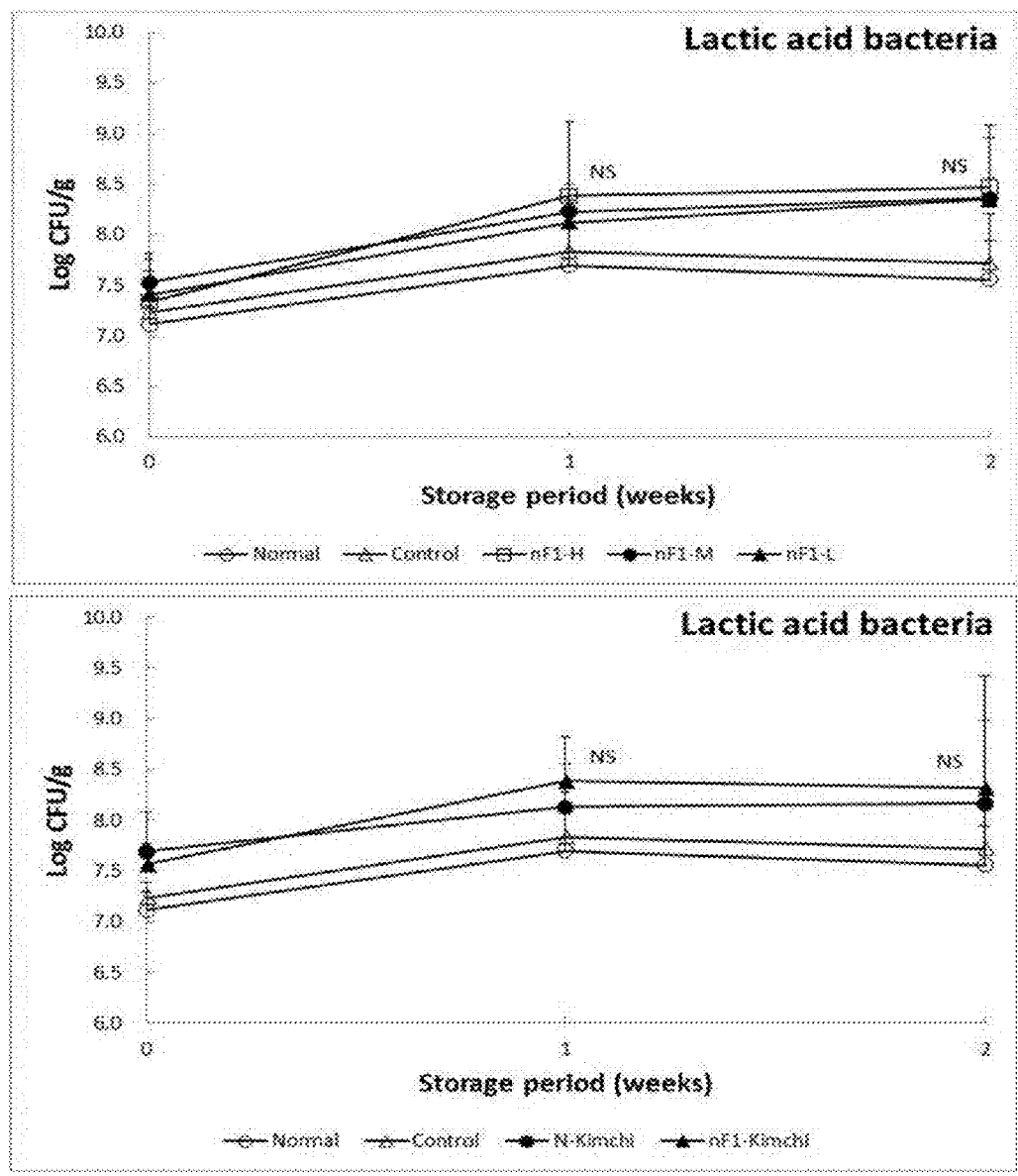
FIG. 13 shows graphs showing counts of intestinal lactic acid bacteria of a colitis-induced mouse.

As shown in FIG. 13, as the result of measuring the number of lactic acid bacteria in feces, it was noted that the number of the lactic acid bacteria varied depending on a test material taken by a mouse. While there were little differences in number of the lactic acid bacteria in the normal group and the control group between before and after administration, the number of lactic acid bacteria in the feces was increased in all of the nF1-administered groups (nF1-H, nF1-M, nF1-L) and in the kimchi-administered groups. Among these groups, the highest increase in number of lactic acid bacteria in the feces was shown in the nF1-H group.

Specifically, after the total two-week administration of a test material, the largest amount of lactic acid bacteria in feces were detected at 8.47±0.09 log CFU/g in the nF1-H group, and thus it seemed that, when a high concentration of nF1 was taken, an effect of increasing lactic acid bacteria in an intestine was shown.

In addition, 2 weeks later, the lactic acid bacteria in the feces of the nF1-Kimchi group were detected at 8.31±1.10 log CFU/g, which was higher than that in the normal kimchi to which nF1 was not added. It showed that, when nF1 was added to kimchi, an effect of increasing lactic acid bacteria in an intestine was shown.

3-8) Measurement of Harmful Enzymes (β-Glucosidase, β-Glucuronidase) in Feces

β-glucosidase and β-glucuronidase secreted through the metabolism of intestinal bacteria are known as harmful enzymes transforming a β-glucoside glycoside compound and a glucuronic acid compound into harmful compounds. Particularly, a representative harmful enzyme in an intestine, β-glucuronidase, generates amines and toxic materials or mutagens to damage an intestinal mucosal membrane, resulting in colitis. Toxic materials absorbed in the intestinal tract are circulated in the body to damage various organs and can lead to cancer, alteriosclerosis, hepatotoxicity, and immunosuppression. Accordingly, the change in activity of harmful enzymes in mouse feces according to the administration of a test material was measured, and the result is shown in FIG. 9.

Specifically, to measure a β-glucosidase activity, 0.1 ml of an enzyme solution was added to 0.3 ml of a 0.1 M sodium phosphate buffer (pH 7.0) and 0.2 ml of 2 mM p-nitrophenyl-β-D-glucopyranoside and reacted at 37° C. for 15 minutes, and then 0.3 ml of 0.5N NaOH was added to end the reaction. Here, 1 ml of distilled water was added, centrifugation was conducted at 3,000 rpm for 20 minutes, and then a supernatant was taken to measure an optical density at 405 nm.

Figure 14:
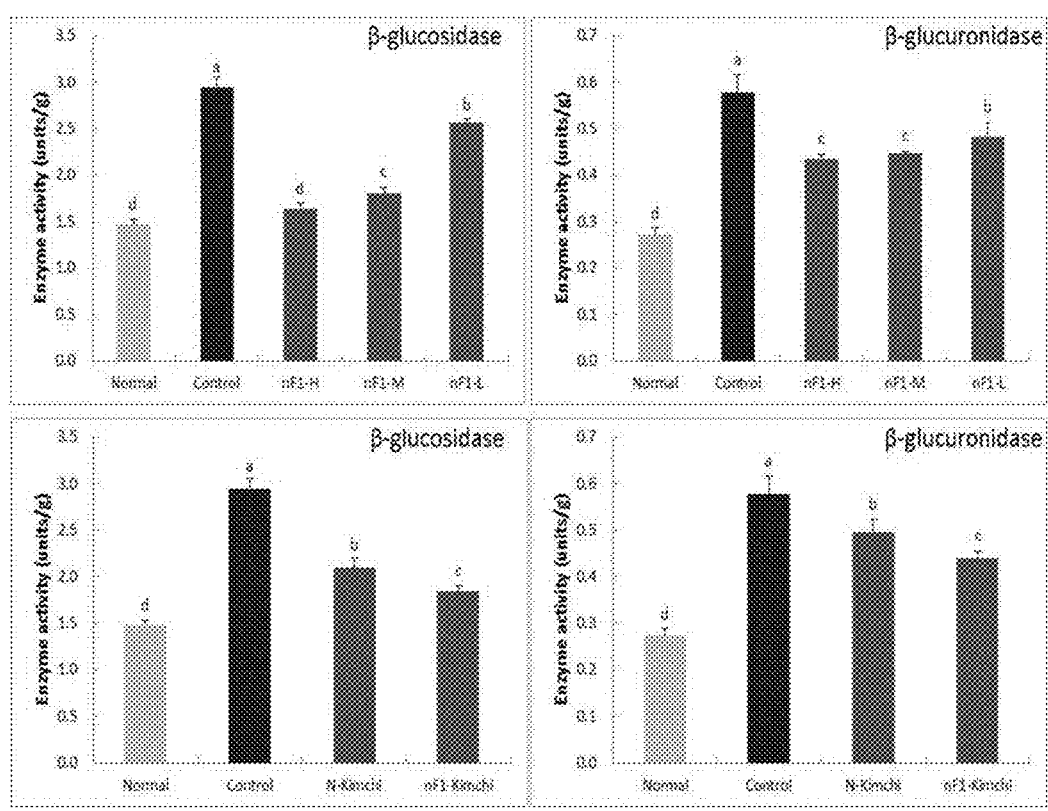
FIG. 14 shows graphs showing activity of a harmful enzyme in the intestine of a colitis-induced mouse.

The β-glucosidase activity of an initial mouse before a test material was administered was 1.11±0.22 units/g, and as shown in FIG. 14, the activity of the normal group after a test material was administered for 2 weeks was 1.48±0.04 units/g, and the activity of the control group was 2.76±0.29 units/g.

Meanwhile, among the nF1-administered mouse groups, the β-glucosidase activity of the nF1-H group was 1.64±0.06 units/g, the β-glucosidase activity of the nF1-M group was 1.81±0.06 units/g, and the β-glucosidase activity of the nF1-L group was 2.57±0.04 units/g, and therefore it was confirmed that, as the nF1 concentration was increased, the β-glucosidase activity was decreased. In addition, the β-glucosidase activity of the nF1-Kimchi group was 1.97±0.23 units/g, and the β-glucosidase activity of the N-Kimchi group was 2.09±0.10 units/g. Therefore, it was noted that nF1-added kimchi exhibited a significantly lower β-glucosidase activity ($p<0.05$).

In addition, to measure a β-glucuronidase activity, 0.1 ml of an enzyme solution was added to 0.38 ml of a 0.1 M sodium phosphate buffer (pH 7.0) and 0.02 ml of 2 mM p-nitrophenyl-β-D-glucuronide and reacted at 37° C. for 1 hour, and then 0.4 ml of 0.5N NaOH was added to end the reaction. Here, 1 ml of distilled water was added, centrifugation was conducted at 3,000 rpm for 20 minutes, and then a supernatant was taken to measure an optical density at 405 nm.

The β-glucuronidase activity of an initial mouse before a test material was not administered was 0.29±0.01, and as shown in FIG. 14, the β-glucuronidase activity of the normal group after a test material was administered for 2 weeks was 0.27±0.01 units/g, and the β-glucuronidase activity of the control group was 0.58±0.04 units/g.

Meanwhile, among the nF1-administered mouse groups, the β-glucuronidase activity of the nF1-H group was 0.44±0.01 units/g, the β-glucuronidase activity of the nF1-M group was 0.44±0.01 units/g, and the β-glucuronidase activity of the nF1-L group was 0.50±0.05 units/g, which showed that the β-glucuronidase activities were low in the high- and medium-concentration groups. In addition, the β-glucuronidase activities were 0.44±0.01 units/g in the nF1-Kimchi group and 0.47±0.05 units/g in the N-Kimchi group, and it was noted that nF1-added kimchi exhibited a significantly lower β-glucuronidase activity ($p<0.05$).

Consequently, when nF1 is taken at a high concentration or nF1 is added to kimchi, the activities of the β-glucosidase and β-glucuronidase enzymes in feces are decreased, and therefore it seems that an environment in a colon is improved by reducing the generation of an intestinal toxic material (conversion of a pro-carcinogen into a carcinogen).

[Accession Number]

Depositary authority: National Institute of Technology and Evaluation (NITE) Patent Microorganisms Depositary (NPMD)

Accession No.: NITE P-1462

Deposit Date: 2012 Nov. 8

The invention claimed is:

1. A method of producing a non-aggregating nano-sized kimchi lactic acid bacteria having a particle size distribution of 0.5 to 1.0 m and a cocci shape, the method comprising:
    culturing a *Lactobacillus plantarum* nF1 strain isolated from kimchi and deposited under the Accession No. NITE P-1462 at a pH of 5 to 7 to prepare a culture solution;
    heating and sterilizing the culture solution at 80° C. for 8 to 12 minutes;
    dispersing the heated and sterilized culture solution by adding an excipient and homogenizing using a high pressure homogenizer at a pressure of 140 to 160 kgf/cm$^2$; and
    freeze-drying the dispersed culture solution to prepare a freeze-dried composition comprising non-aggregating nano-sized *Lactobacillus plantarum* nF1 strain (NITE P-1462).

2. The method of claim 1, further comprising:
    isolating the *Lactobacillus plantarum* strain of claim 1 from kimchi.

3. A freeze-dried composition comprising a non-aggregating nano-sized *Lactobacillus plantarum* nF1 strain deposited under the accession No. NITE P-1462 prepared by nanonizing *Lactobacillus plantarum* nF1 strain (NITE P-1462) isolated from kimchi, and having a particle size distribution of 0.5 to 1.0 micrometer and a cocci shape;
    wherein the nanonizing comprises:
    culturing the *Lactobacillus plantarum* nF1 strain at a pH of 5 to 7 to prepare a culture solution;
    heating and sterilizing the culture solution at 80° C. for 8 to 12 minutes;
    dispersing the heated and sterilized culture solution by adding an excipient and homogenizing using a high pressure homogenizer at a pressure of 140 to 160 kgf/cm$^2$; and
    freeze-drying the dispersed culture solution to provide said composition comprising non-aggregating nano-sized *Lactobacillus plantarum* nF1 strain (NITE P-1462).

4. The composition of claim 3, wherein the *Lactobacillus plantarum* nF1 strain has a 16S rRNA sequence represented by SEQ. ID. NO. 1.

5. The composition of claim 3, wherein the composition includes $10^{12}$ to $5 \times 10^{12}$ cfu/g of the *Lactobacillus plantarum* nF1 strain.

6. A food additive, comprising: the non-aggregating nano-sized *Lactobacillus plantarum* nF1 strain (NITE P-1462) composition of claim 3.

7. A functional food, comprising: the non-aggregating nano-sized *Lactobacillus plantarum* nF1 strain (NITE P-1462) composition of claim 3.

8. A pharmaceutical composition for preventing and treating a colorectal disease, comprising: the non-aggregating nano-sized *Lactobacillus plantarum* nF1 strain (NITE P-1462) composition of claim 3 as an active ingredient.

9. A health functional food composition for preventing and treating a colitis disease, comprising: the non-aggregating nano-sized *Lactobacillus plantarum* nF1 strain (NITE P-1462) composition of claim 3.

10. The composition of claim 8, wherein the colorectal disease is colitis or colorectal cancer.

* * * * *

SEQUENCE LISTING

<160> NUMBER OF SEQ ID NOS: 3

<210> SEQ ID NO 1
<211> LENGTH: 1492
<212> TYPE: DNA
<213> ORGANISM: Artificial Sequence
<220> FEATURE:
<223> OTHER INFORMATION: 16S rRNA of Lactobacillus plantarum gene nF1

<400> SEQUENCE: 1

```
gacgaacgct ggcggcgtgc ctaatacatg caagtcgaac gaactctggt attgattggt      60
gcttgcatca tgatttacat ttgagtgagt ggcgaactgg tgagtaacac gtgggaaacc     120
tgcccagaag cgggggataa cacctggaaa cagatgctaa taccgcataa caacttggac     180
cgcatggtcc gagcttgaaa gatggcttcg gctatcactt ttggatggtc ccgcggcgta     240
ttagctagat ggtggggtaa cggctcacca tggcaatgat acgtagccga cctgagaggg     300
taatcggcca cattgggact gagacacggc ccaaactcct acgggaggca gcagtaggga     360
atcttccaca atggacgaaa gtctgatgga gcaacgccgc gtgagtgaag aagggtttcg     420
gctcgtaaaa ctctgttgtt aaagaagaac atatctgaga gtaactgttc aggtattgac     480
ggtatttaac cagaaagcca cggctaacta cgtgccagca gccgcggtaa tacgtaggtg     540
gcaagcgttg tccggattta ttgggcgtaa agcgagcgca ggcggttttt taagtctgat     600
gtgaaagcct tcggctcaac cgaagaagtg catcggaaac tgggaaactt gagtgcagaa     660
gaggacagtg gaactccatg tgtagcggtg aaatgcgtag atatatggaa gaacaccagt     720
ggcgaaggcg gctgtctggt ctgtaactga cgctgaggct cgaaagtatg ggtagcaaac     780
aggattagat accctggtag tccataccgt aaacgatgaa tgctaagtgt tggagggttt     840
ccgcccttca gtgctgcagc taacgcatta agcattccgc ctggggagta cggccgcaag     900
gctgaaactc aaaggaattg acggggggccc gcacaagcgg tggagcatgt ggtttaattc     960
gaagctacgc gaagaacctt accaggtctt gacatactat gcaaatctaa gagattagac    1020
gttcccttcg gggacatgga tacaggtggt gcatggttgt cgtcagctcg tgtcgtgaga    1080
tgttgggtta agtcccgcaa cgagcgcaac ccttattatc agttgccagc attaagttgg    1140
gcactctggt gagactgccg gtgacaaacc ggaggaaggt ggggatgacg tcaaatcatc    1200
atgcccctta tgacctgggc tacacacgtg ctacaatgga tggtacaacg agttgcgaac    1260
tcgcgagagt aagctaatct cttaaagcca ttctcagttc ggattgtagg ctgcaactcg    1320
cctacatgaa gtcggaatcg ctagtaatcg cggatcagca tgccgcggtg aatacgttcc    1380
cgggccttgt acacaccgcc cgtcacacca tgagagtttg taacacccaa agtcggtggg    1440
```

```
gtaacctttt aggaaccagc cgcctaaggt gggacagatg attagggtga ag            1492
```

<210> SEQ ID NO 2
<211> LENGTH: 19
<212> TYPE: DNA
<213> ORGANISM: Artificial Sequence
<220> FEATURE:
<223> OTHER INFORMATION: forward primer

<400> SEQUENCE: 2

```
gagtttgatc ctggctcag                                                  19
```

<210> SEQ ID NO 3
<211> LENGTH: 16
<212> TYPE: DNA
<213> ORGANISM: Artificial Sequence
<220> FEATURE:
<223> OTHER INFORMATION: reverse primer

<400> SEQUENCE: 3

```
tcgtaacaag gtagcc                                                     16
```